(12) United States Patent
Ueno et al.

(10) Patent No.: US 10,967,201 B2
(45) Date of Patent: Apr. 6, 2021

(54) RADIATION MONITOR AND METHOD OF MONITORING RADIATION

(71) Applicant: HITACHI, LTD., Tokyo (JP)

(72) Inventors: Yuichiro Ueno, Tokyo (JP); Takahiro Tadokoro, Tokyo (JP); Yasushi Nagumo, Tokyo (JP); Shuichi Hatakeyama, Tokyo (JP); Katsunori Ueno, Tokyo (JP); Kouichi Okada, Tokyo (JP)

(73) Assignee: HITACHI, LTD., Tokyo (JP)

( * ) Notice: Subject to any disclaimer, the term of this patent is extended or adjusted under 35 U.S.C. 154(b) by 0 days.

(21) Appl. No.: 16/340,696

(22) PCT Filed: Dec. 15, 2017

(86) PCT No.: PCT/JP2017/045052
§ 371 (c)(1),
(2) Date: Apr. 10, 2019

(87) PCT Pub. No.: WO2018/116969
PCT Pub. Date: Jun. 28, 2018

(65) Prior Publication Data
US 2019/0290935 A1      Sep. 26, 2019

(30) Foreign Application Priority Data
Dec. 22, 2016  (JP) .............................. JP2016-249870

(51) Int. Cl.
*H01S 3/0955*  (2006.01)
*G01T 1/20*  (2006.01)
(Continued)

(52) U.S. Cl.
CPC ............. *A61N 5/1071* (2013.01); *A61N 5/10* (2013.01); *G01T 1/20* (2013.01); *H01S 3/0955* (2013.01);
(Continued)

(58) Field of Classification Search
CPC .................... A61N 5/10; A61N 5/1071; A61N 2005/1087; A61N 2005/109; G01T 1/20; H01S 3/0955; H01S 3/1611; H01S 3/1643
See application file for complete search history.

(56) References Cited

U.S. PATENT DOCUMENTS 9,068,111 B2 *   6/2015   Ohashi ................... C04B 35/117
2015/0123002 A1 *   5/2015   Ueno ........................ G01T 1/10
                                                                 250/362

FOREIGN PATENT DOCUMENTS

JP       2001-56381 A     2/2001
JP       2013-134157 A    7/2013

OTHER PUBLICATIONS

International Search Report PCT/JP2017/045052 dated Mar. 6, 2018.

* cited by examiner

*Primary Examiner* — David P Porta
*Assistant Examiner* — Fani P Boosalis
(74) *Attorney, Agent, or Firm* — Mattingly & Malur, PC

(57) ABSTRACT

A radiation monitor 1 includes a light-emitting unit 10 which generates light having an intensity depending on an amount of an incident radiation, an optical fiber 20 which sends a photon generated by the light-emitting unit 10, a photoelectric converter 30 which transmits one electric pulse to one sent photon, a dose calculation device 40 which counts the electric pulse amplified by the photoelectric converter 30 and converts the counted value of the measured electric pulses into a dose of the radiation, and a display device 50. The dose calculation device 40 counts the electric signals converted from the photon by the photoelectric converter 30 to calculate a counting rate, and stops the counting when the counting rate exceeds a predetermined threshold, and per- (Continued)

forms counting when the counting rate is less than the threshold.

9 Claims, 7 Drawing Sheets

(51) Int. Cl.
 *A61N 5/10* (2006.01)
 *H01S 3/16* (2006.01)
(52) U.S. Cl.
 CPC .......... *H01S 3/1611* (2013.01); *H01S 3/1643* (2013.01); *A61N 2005/109* (2013.01); *A61N 2005/1087* (2013.01); *A61N 2005/1089* (2013.01)

ENERGY LEVEL $Eo < Ei$
$\lambda o > \lambda i$ $\lambda i < \lambda c < \lambda o$

ENERGY LEVEL

RADIATION MONITOR AND METHOD OF MONITORING RADIATION

TECHNICAL FIELD

The invention relates to an fiber optic radiation monitor which is suitable to a radiotherapy device, and a method of monitoring a radiation.

BACKGROUND ART

PTL 1 discloses a dosimeter "including a scintillation fiber which irradiates light when a radiation is incident, an optical transmission fiber which sends the light from the scintillation fiber, a band pass filter which removes noises generated when the radiation is incident on the optical transmission fiber and passes light having a specific frequency, and an optical detection unit which detects the light sent through the band pass filter" is a local dosimeter which can perform the measurement with high accuracy by removing noises generated when the radiation is incident to the optical transmission unit at the time of measuring the radiation in a body (in particular, the Cherenkov radiation) in brachytherapy in which a radioactive small source is inserted into a body for therapy.

CITATION LIST

Patent Literature

PTL 1: JP 2001-56381 A

SUMMARY OF INVENTION

Technical Problem

The leading cause of death in Japan is cancer and the number of deaths continues to increase. In recent years, in Japan, where quality of life (QOL) needs to be improved, radiation cancer treatment is attracting attention as a treatment for cancer. With the increase in the accuracy of cancer radiation therapy technology, which is a seed, cancer radiation therapy has started to spread widely in Japan in response to the improvement of QOL as a need.

There are Various kinds of radiation include X-rays, electron beams, proton beams, heavy particle rays, neutron rays, etc. in radiations used for treatment. In recent years, the development of therapeutic devices using proton beams and heavy particle beams has been particularly remarkable.

These proton beams and heavy particle beams have a property of producing a peak of dose (Bragg peak) by intensively giving energy just before stopping. Therefore, with this property, the radiation dose can be made concentrated on a cancer region, and the treatment with minimally invasion and high accuracy can be expected.

In addition, in X-ray therapy, Intensity Modulated Radiation Therapy (IMRT) and Image Guided Radiation Therapy (IGRT) are developed and efforts have been made to concentrate the dose on the cancer region.

With the advancement of the radiotherapy device, a total accuracy related to radiotherapy such as the treatment planning, the accuracy of patient positioning, and the measurement of the dose rate for quality assurance (QA) of the treatment planning and device is required to improve.

An ionization chamber with good stability and reproducibility is widely used for measuring a dose in radiotherapy. The miniaturization of the ionization chamber is limited by its detection principle, and dose distribution measurement using a semiconductor detector which is relatively easily miniaturized is performed instead. However, if a signal processing system is also included, miniaturization of the semiconductor detector is limited. In addition, these detectors need to feed a high voltage for measurement, and there is a problem that it is difficult to measure the dose by inserting them into the body. Further, these detectors are generally high in density, and the interaction with radiation is large compared with the material in the body and water, and thus there is a problem that the influence of the detector itself cannot be ignored.

As described above, in a situation where an actual dose absorbed in a body is not able to be grasped, the dose distribution in the treatment planning has a margin in consideration of a body movement, which prevents the further improvement in the accuracy of the radiation. In addition, in a case where a normal portion sensitive to the radiation is near a portion to be treated, the radiotherapy is hard to do, and it is desired to grasp the dose absorbed in the body.

It is desired that the dosimeter is installed in the body to directly measure the dose in the body during irradiating the radiation. A compact small-sized fiber type dosimeter having a minimally invasion property is desirable. However, if a high-speed electron generated by irradiating the radiation enters the optical fiber, the Cherenkov radiation is generated. Therefore, the generation of the Cherenkov radiation during the radiation is a problem in an fiber optic dosimeter.

In response to such a problem, there is a technique disclosed in PTL 1 as a technique in brachytherapy in which a radioactive small source is inserted into the body for therapy.

On the other hand, since a high-intensity radiation is irradiated in a short time in X-ray, electron beam, and proton beam therapy of high energy in particular, the Cherenkov radiation to be generated is also enlarged. Therefore, in radiotherapy using such an accelerator, the effect of noise reduction method by an optical filter described in PTL 1 is not sufficient, and further reduction of Cherenkov radiation is desired.

Thus, in order to measure the dose in the body, it is very important that the dosimeter is small and less invasive, and the influence of Cherenkov radiation generated in the optical fiber is reduced, as described above.

An object of the invention is to provide a small and minimally invasive radiation monitor which can reduce the influence of the Cherenkov radiation generated in an optical fiber and measure a dose in a body in real time and a method of monitoring a radiation.

Solution to Problem

In order to solve the above problem, the configurations disclosed in claims are employed for example.

The invention includes a plurality of means to solve the above problem. As an example of the means, there is a radiation monitor which includes: a light-emitting unit which generates light having an intensity depending on an amount of incident radiation; an optical fiber which sends a photon generated by the light-emitting unit; a photoelectric converter which converts the photon sent by the optical fiber into an electric signal; a dose calculation device which calculates a dose from the electric signal converted by the photoelectric converter, detects a radiation timing and calculates a dose of the radiation on the basis of the detected timing; and a display device which displays a measurement result calculated by the dose calculation device.

Advantageous Effects of Invention

According to the invention, a small and minimally invasive dosimeter makes it possible to reduce the influence of the Cherenkov radiation generated in an optical fiber, and to measure a dose in a body in real time.

DESCRIPTION OF EMBODIMENTS

Hereinbelow, modes (hereinafter, referred to as "embodiments") for carrying out a radiation monitor and a method of monitoring the radiation of the invention will be described in detail with reference to the drawings appropriately.

First Embodiment

Figure 1:
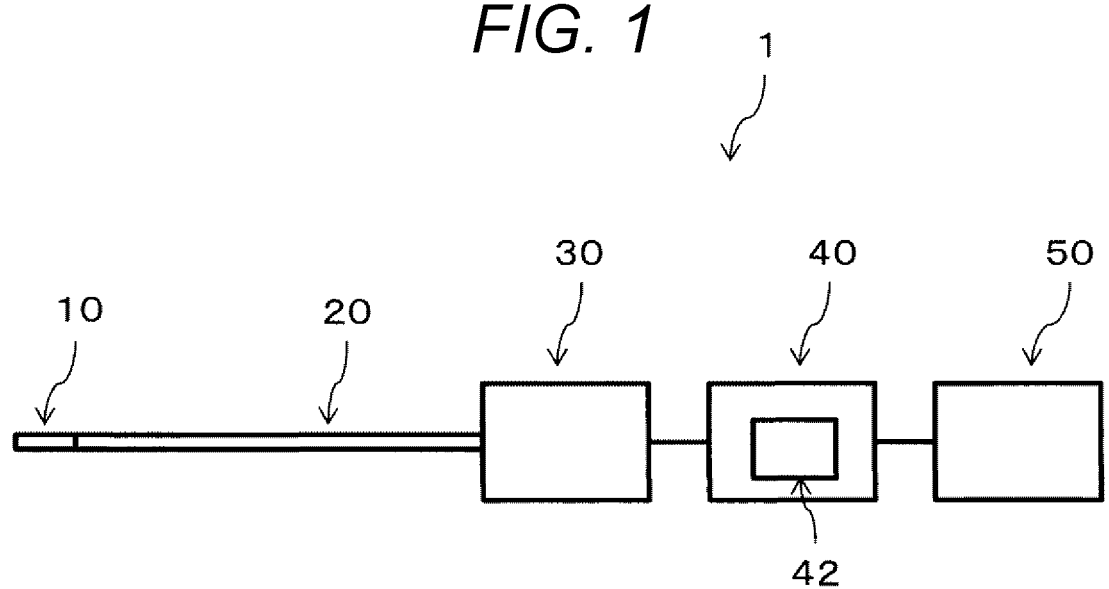
FIG. 1 is a diagram illustrating a configuration of a radiation monitor according to a first embodiment.
Figure 2:
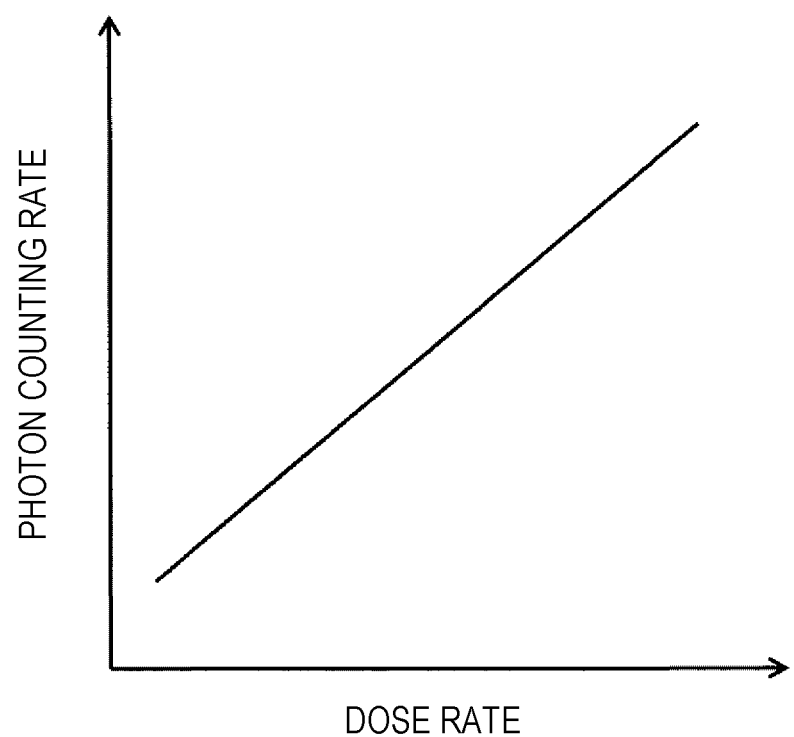
FIG. 2 is a diagram illustrating a relation between a dose rate and a photon counting rate according to the first embodiment.
Figure 3:
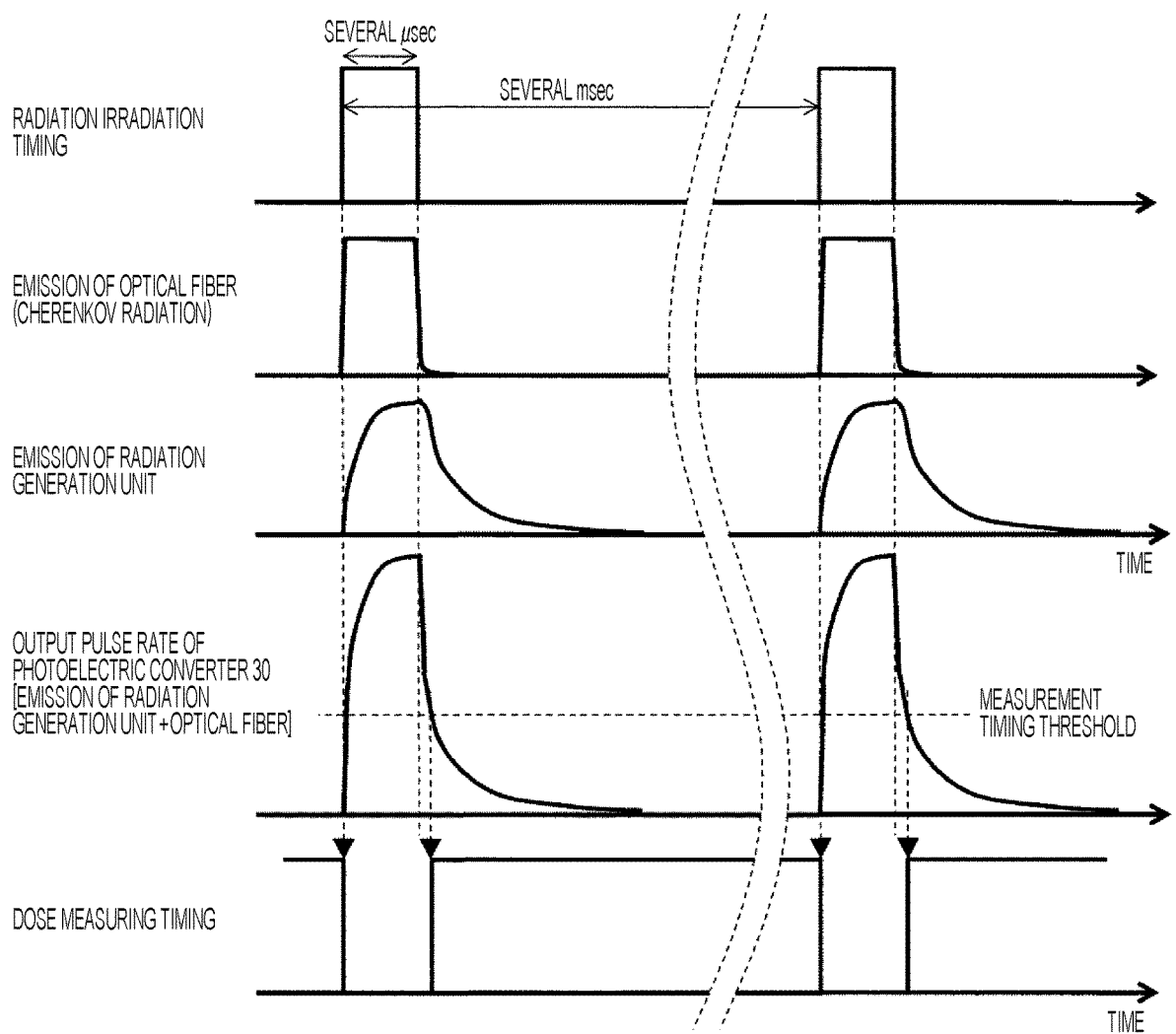
FIG. 3 is a timing chart of a radiation timing, the Cherenkov radiation, an emission state of a light-emitting unit, and the like according to the first embodiment.

A radiation monitor according to a first embodiment will be described using FIGS. 1 to 3. FIG. 1 is a diagram of a configuration of a radiation monitor 1 according to this embodiment. FIG. 2 is a diagram illustrating a relation between a dose rate and a photon counting rate. FIG. 3 is a timing chart of a radiation timing, the Cherenkov radiation, an emission state of a light-emitting unit, and the like.

In FIG. 1, the radiation monitor 1 is configured to include a light-emitting unit 10, an optical fiber 20, a photoelectric converter 30, a dose calculation device 40, and a display device 50.

The light-emitting unit 10 is made of a light-emitting material which generates light having an intensity depending on a dose of an incident radiation. The light-emitting material contains at least one of rare earth elements. Specifically, the light-emitting material is configured by a material such as transparent yttrium, aluminum, and garnet as a base material, and a rare earth element such as ytterbium, neodymium, cerium, and praseodymium which are contained in the material.

In this way, the light-emitting material contains at least one of rare earth elements, so that a linearity between the dose rate of the radiation incident on the light-emitting unit 10 and the intensity of the light can be improved. The radiation monitor 1 can measure the dose rate of the radiation with more accuracy even when the high dose rate radiation is incident.

Further, the light-emitting unit 10 is not limited to the above configuration. A light-emitting material having a different composition may be used.

The optical fiber 20 is connected to the light-emitting unit 10, and sends generated photons to the photoelectric converter 30 connected on the other side. As a material of the optical fiber 20, for example, quartz and plastic may be included. A flexible material is better in terms of convenience of handling, but a radiation-resistant performance is also desirably considered. In addition, a fiber cover may be provided for the purpose of blocking light while not described in detail.

The photoelectric converter 30 is a converter which is connected to an end of the optical fiber 20 on the side opposite to the connection end of the light-emitting unit 10, and transmits one electric pulse with respect to one sent photon. Examples of the photoelectric converter 30 may include a Photomultiplier tube and an avalanche photodiode. With these Photomultiplier tubes, the photon can be amplified in current and converted into an electric pulse. In addition, while not specifically described, there may be provided an amplifier which amplifies the output signal from the photoelectric converter 30 and shapes the waveform of the output signal as needed.

The dose calculation device 40 is connected to the photoelectric converter 30, counts the electric pulses amplified by the photoelectric converter 30, converts the counted value of the measured electric pulses into a dose of the radiation, and outputs a display signal to the display device 50. In the dose calculation device 40 of this embodiment, as a control of addition timing of the counting used in the calculation of a dose, an electric signal converted by the photoelectric converter 30 from each one of the photon is counted one by one to calculate a counting rate, the counting rate is compared with a predetermined threshold (measurement timing threshold) to detect the radiation timing. The counting is stopped during a period when the counting rate exceeds the measurement timing threshold, and the counting starts when the counting rate becomes equal to or less than the threshold. The details will be described below.

The inventors have found experimentally that there is a one-to-one correspondence between the dose rate of the incident radiation and the number of photons (hereinafter, also referred to as "counting rate of photon") which are generated per unit time by the light-emitting unit 10 as illustrated in FIG. 2. On the other hand, it is well known that there is a one-to-one correspondence between the counting rate of the photon and the counting rate of the electric pulse. Therefore, it is derived that there is also a one-to-one correspondence between the dose rate of the radiation and the counting rate of the electric pulse. With this relation, the counting rate of the obtained electric pulse can be converted into the dose rate of the radiation.

Specifically, the dose calculation device 40 includes a memory device 42 which stores a data table to associate the counted value of the electric pulse with the dose of the radiation therein. The dose calculation device performs a calculation process to convert the counted value of the electric pulse using the data table into the dose of the radiation. Herein, in the dose calculation device 40, the counted value and the dose may be converted into the counting rate and the dose rate which are values per unit time, and may use the data table of any conversion. In addition, the correspondence between the dose rate of the radiation and the counting rate of the electric pulse differs depending on the size, the shape, the material of the light-emitting unit 10 to be used, and the thickness and the length of the optical fiber 20. Therefore, the correspondence is obtained in advance for each radiation monitor 1 to put it in a data table, so that the counting rate of the obtained electric pulse can be converted into the dose rate of the radiation. Further, a factor to be derived using the dose calculation device 40 is not limited to the dose rate (dose) of the radiation, and a change with time of the dose rate or the like may be derived.

The display device 50 receives the display signal from the dose calculation device 40, and displays the dose and the dose rate calculated by the dose calculation device 40. Of course, the display device 50 can also displays relevant information such as a measurement time and various type of measurement conditions.

Next, the radiation, emission of the light-emitting unit 10, and a light-emission timing of the Cherenkov radiation from the optical fiber 20 will be described using FIG. 3.

For example, in the case of an X-ray therapeutic device, the X ray is irradiated in a pulse shape with several µsec width in a several msec period. The Cherenkov radiation is generated when a high-speed electron moves in the optical fiber 20, and generated in synchronization with the radiation. On the other hand, the emission of the light-emitting unit 10 has a feature that the light can be seen even after emission because of a fluorescence lifetime depending on the material.

Then, if the emission of the light-emitting unit 10 is measured immediately after the irradiation while not performing the measurement during the radiation, the influence of the Cherenkov radiation can be removed from the measurement.

Specifically, in this embodiment, as illustrated in an output pulse rate of the photoelectric converter 30 of FIG. 3, the measurement is stopped during a period when the counting rate measured by the dose calculation device 40 exceeds a predetermined threshold (measurement timing threshold) (the addition of the pulse counting is stopped), and the counting may start when the counting rate is equal to or less than the threshold.

A determination method of the measurement timing is not limited to the above method. For example, the measurement timing threshold can be changed according to an intensity of irradiation dose of the radiation and a length of an irradiation field of the optical fiber 20. In addition, the determination is performed not by the counting rate but by a derivative of the counting rate (that is, a difference in the counted value in the interval of measurement times). If the derivative is equal to or more than a specific threshold, the measurement is stopped. If the derivative is equal to or less than the threshold, the measurement starts. The important thing is that an emission timing of the Cherenkov radiation can be found.

Next, effects of this embodiment will be described.

As described above, the generation timing of the Cherenkov radiation is determined from the measured counting rate by the dose calculation device 40. The influence of the Cherenkov radiation, which is noise, can be removed from the measurement by stopping the measurement during a period when the Cherenkov radiation is generated. Therefore, it is possible to significantly improve the accuracy. In addition, according to the configuration of this device, there is no need to add a specific measurement device to a fiber optic dosimeter. It is possible to realize a simple measurement system, that is, a low cost of the measurement device. With these effects, the influence of the Cherenkov radiation can be reduced, and the dose rate in a body during the radiotherapy can be measured in real time and the radiation for a Quality Control (QA/QC) of a therapeutic device can be measured with high accuracy.

Therefore, with such a device, the influence of a body movement and the influence of a change with time of an organ are reduced, so that the dose can be irradiated with high accuracy. In addition, the irradiation dose onto a normal portion is reduced, and an improvement in the radiotherapy such as expanding a range of adaptation of the radiotherapy can be also realized.

Second Embodiment

A radiation monitor according to a second embodiment will be described using FIGS. 4 and 5. The same configurations as those of the first embodiment will be attached with the same symbol, and the description thereof will be omitted. The following embodiments are also the same.

Figure 4:
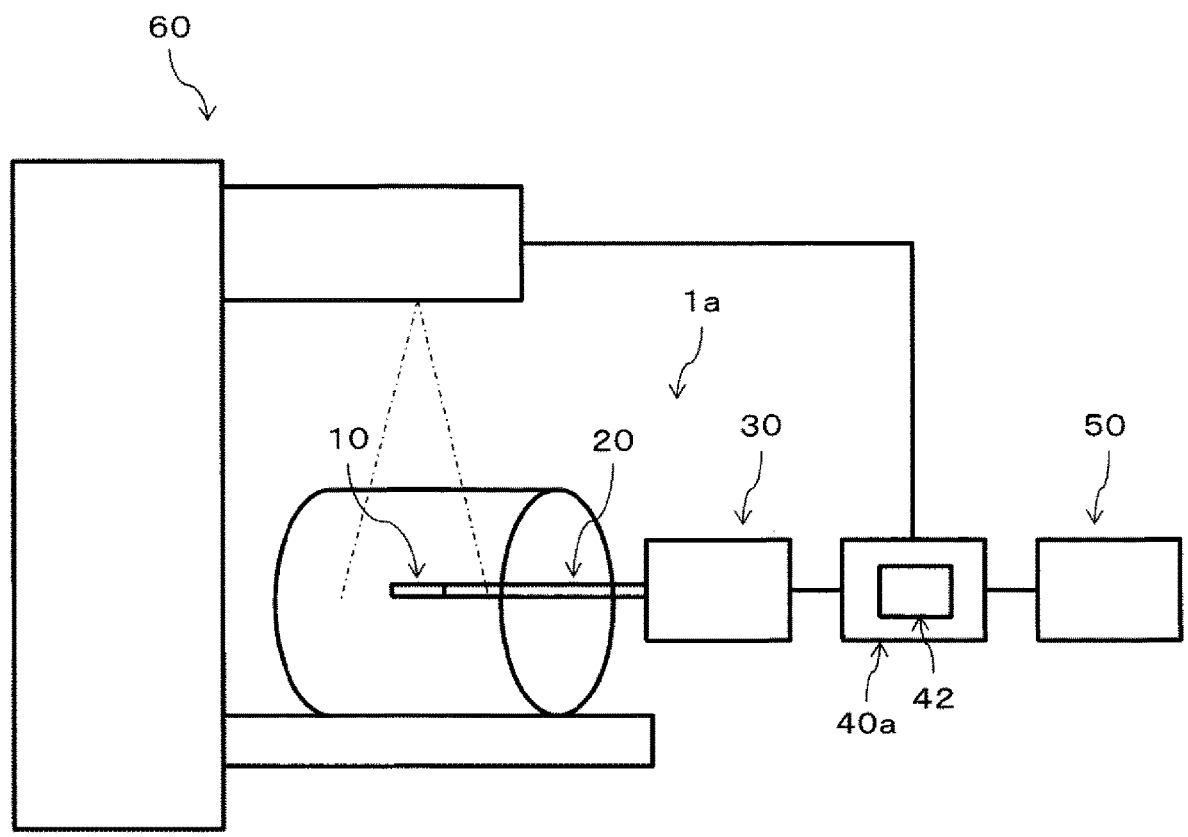
FIG. 4 is a diagram illustrating a configuration of a radiation monitor according to a second embodiment.

FIG. 4 is a diagram of a configuration of a radiation monitor according to this embodiment. FIG. 5 is a timing chart of a radiation timing, the Cherenkov radiation, an emission state of a light-emitting unit, and the like according to this embodiment.

As illustrated in FIG. 4, a radiation monitor 1a of this embodiment is configured to include the light-emitting unit 10, the optical fiber 20, the photoelectric converter 30, a dose calculation device 40a, and the display device 50. This embodiment is different from the radiation monitor 1 of the first embodiment in that the dose calculation device 40a detects the radiation timing by receiving a radiation timing signal from a radiation irradiation device 60 which irradiates the radiation to control a timing for measuring as a control of addition timing of the counting used in calculation of the dose. Therefore, in the following, only the dose calculation device 40a will be described in detail. The other configurations and operations are almost the same as those of the radiation monitor 1 of the first embodiment, and details thereof will be omitted.

The radiation and a dose measuring timing in this embodiment will be described using FIG. 5. In the dose calculation device 40a, a signal related to the radiation timing from the radiation irradiation device 60 is received, and the emission of the light-emitting unit 10 is measured at the dose measuring timing except the radiation timing.

According to the radiation monitor of this embodiment, the influence of the Cherenkov radiation can be removed similarly to the radiation monitor of the first embodiment. Furthermore, in the first embodiment, there is a concern that a time lag occurs from the end of irradiation until the measurement starts and causes a fail to acquire effective data. However, in this embodiment, an irradiation timing signal from the radiation irradiation device 60 is acquired, so that the time lag is reduced and the failure is reduced, and the improvement effects of measurement sensitivity and the accuracy can be obtained.

Third Embodiment

Figure 6:
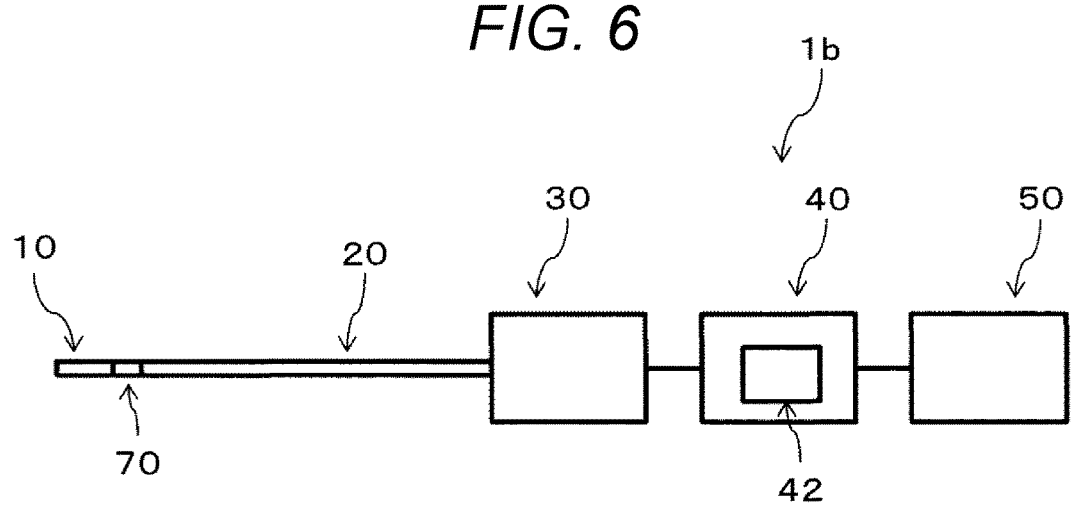
FIG. 6 is a diagram illustrating a configuration of a radiation monitor according to a third embodiment.

A radiation monitor according to a third embodiment will be described using FIG. 6. FIG. 6 is a diagram of a configuration of a radiation monitor according to this embodiment.

A radiation monitor 1b of this embodiment illustrated in FIG. 6 is different from the radiation monitor 1 of the first embodiment in that an optical filter 70 is provided between the light-emitting unit 10 and the optical fiber 20. The other configurations and operations are almost the same, and the description thereof will be omitted. In addition, similarly, this embodiment is different from the radiation monitor 1a of FIG. 4 according to the second embodiment in that the optical filter 70 is provided between the light-emitting unit 10 and the optical fiber 20. Therefore, the optical filter 70 will be described in detail below.

In the first and second embodiments, the measurement is stopped at the timing when the Cherenkov radiation is generated, so that a direct influence thereof can be removed. However, the generated Cherenkov radiation is incident also on the light-emitting unit 10 to excite the light-emitting unit 10 to emit light. The emission of the light-emitting unit 10 by the Cherenkov radiation cannot be differentiated from the emission by the radiation. Therefore, the emission is measured as irremovable noises after the radiation, and thus there is a room for accuracy improvement.

Thus, in this embodiment, with the optical filter 70 provided between the light-emitting unit 10 and the optical fiber 20, the Cherenkov radiation from the optical fiber 20 to the light-emitting unit 10 is removed. Since the optical filter 70 needs to pass the emission of the light-emitting unit 10 and block the Cherenkov radiation, a band pass filter which passes only the emission wavelength of the light-emitting unit 10 is desirable.

According to the radiation monitor of the third embodiment, the direct influence of the Cherenkov radiation can be removed similarly to the radiation monitor of the first and second embodiments. Furthermore, it is possible to remove the emission component of the light-emitting unit by the Cherenkov radiation which is not able to be removed in the radiation monitors of the first and second embodiments. The noises can be further reduced and measurement with higher accuracy is possible.

Fourth Embodiment

Figure 7:
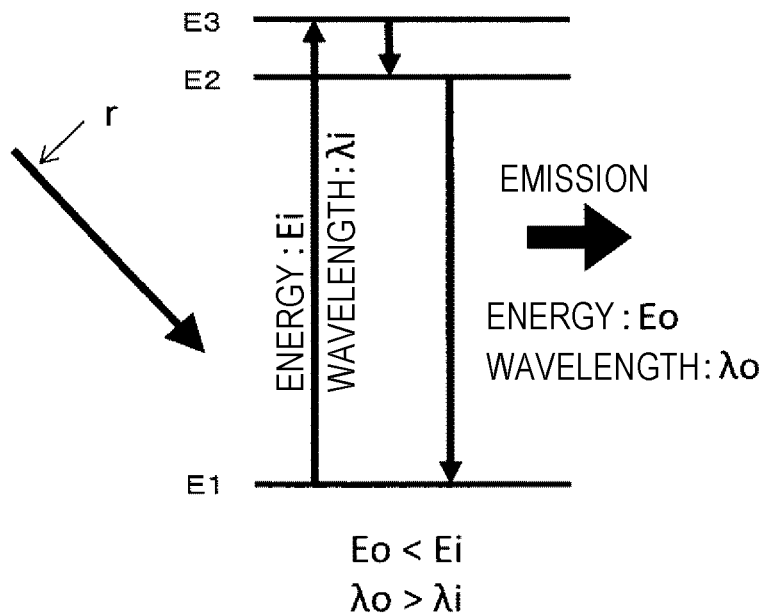
FIG. 7 is a conceptual diagram illustrating a procedure of generating a photon using a radiation incident on an emission unit according to the third embodiment.
Figure 8:
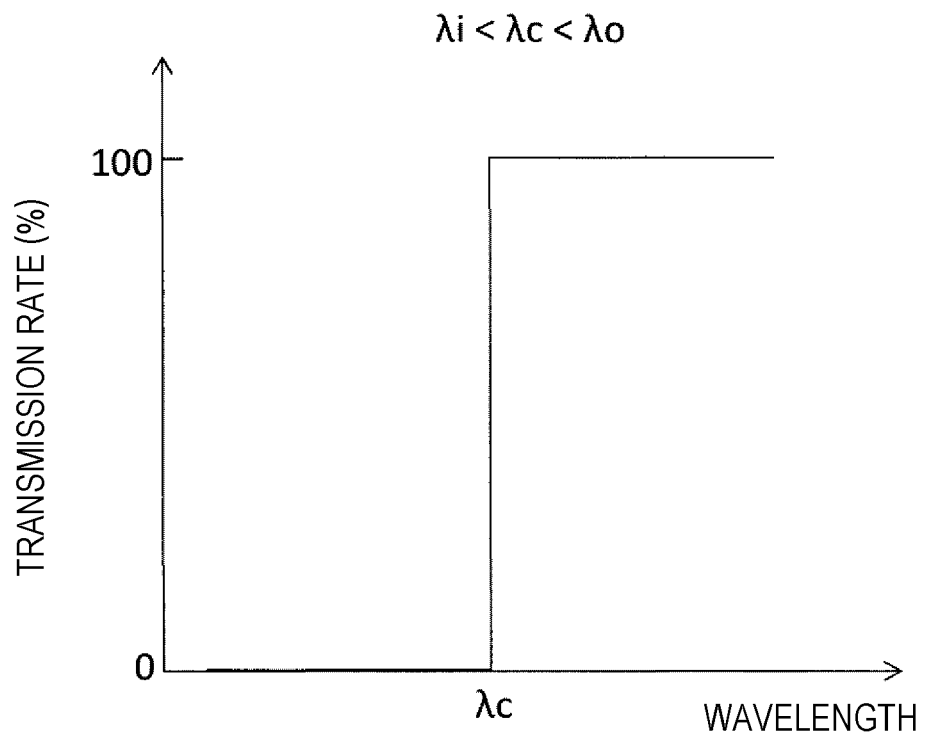
FIG. 8 is a diagram illustrating a wavelength transmission characteristic of an optical filter according to a fourth embodiment.

A radiation monitor according to a fourth embodiment will be described using FIGS. 7 and 8. FIG. 7 is a conceptual diagram illustrating a procedure of generating a photon using a radiation incident on an emission unit according to this embodiment. FIG. 8 is a diagram illustrating a wavelength transmission characteristic of an optical filter according to this embodiment.

The configuration of the radiation monitor in this embodiment is the same as that of the third embodiment. This embodiment is different from the third embodiment only in the characteristic of the optical filter 70, and the description will be given in detail only about the characteristic of the optical filter 70.

Before describing the characteristic of the optical filter 70, the energy level of the light-emitting unit 10 and the emission mechanism will be described using FIG. 7.

When a radiation r is absorbed to the light-emitting unit 10, and the electron in a ground state (E1) obtains energy (Ei), the electron is excited to an energy state E3 as illustrated in FIG. 7. It is assumed that the electron in the energy state E3 is shifted to an energy state E2 without emission for example, and the electron emits light when shifting to the ground state. Then, the emission energy (Eo) should be equal to or less than the energy Ei required for excitation. In other words, an emission wavelength ($\lambda$o) is equal to or longer than an absorption wavelength ($\lambda$i).

Then, the optical filter 70 is desirably a long pass filter (a filter passing a long wavelength band) which has a blocking wavelength longer than the absorption wavelength of the light-emitting unit 10 and shorter than the emission wavelength thereof as illustrated in FIG. 8, in order to block the absorption wavelength of the light-emitting unit 10 of the Cherenkov radiation and to pass only the emission wavelength of the light-emitting unit 10.

According to the radiation monitor of the fourth embodiment, almost the same effect as the radiation monitor of the third embodiment is obtained.

Fifth Embodiment

A radiation monitor according to a fifth embodiment will be described.

The radiation monitor in this embodiment has the same basic configuration as the radiation monitor of any one of the first to fourth embodiments. This embodiment is different from these embodiments only in the fluorescence lifetime of the light-emitting unit 10, and the description will be given in detail only about the characteristic of the light-emitting unit 10.

In the following, the fluorescence lifetime of the light-emitting unit 10 and the emission intensity at the measurement timing are considered.

In an X-ray therapy, the electron is accelerated by an accelerator to irradiate an X ray, and the emission time is several µsec and the period is several msec. Therefore, the measurement time is about 1,000 times the emission time, and the emission (irradiation) time of the light-emitting unit 10 can be approximately considered as zero. In addition, the fluorescence lifetime of the light-emitting unit 10 is set to $\tau$, the pulse length of the radiation is set to Tp, and the pulse interval is set to Ts.

As a first condition of the fluorescence lifetime, the emission of the light-emitting unit 10 caused by the pulse irradiation needs to be sufficiently reduced at the time of the next radiation pulse irradiation. Specifically, if there are n time pulse irradiations during the shortest treatment time, and there is a measurement error within a %, the following conditional expression is obtained where $n\exp(-Ts/\tau) < a$.

$$\tau < Ts/\ln(n/a) \quad (1)$$

Herein, it is desirable that the pulse interval Ts is a length of 10 msec at maximum, the pulse irradiation time n is one time at minimum, and the measurement error a is 3% even when the allowable error of the obtained dose is maximum. With Expression (1), the fluorescence lifetime T of the light-emitting unit 10 is desirably equal to or less than 2.8 msec.

As a second condition of the fluorescence lifetime, the emission amount after the pulse length Tp is b % of the total emission amount. The following conditional expression is obtained where $\exp(-Tp/\tau) > b$.

$$\tau > Tp/\ln(1/b) \quad (2)$$

Herein, the pulse length Tp is 1 psec at minimum, and the required emission ratio b is at least 10%. With Expression (2), the fluorescence lifetime $\tau$ of the light-emitting unit 10 is desirably equal to or more than 430 nsec.

In the radiation monitor of the fifth embodiment, the fluorescence lifetime τ of the light-emitting unit 10 is set to be equal to or less than 2.8 msec, so that the measurement error caused by the remaining light can be set to 3% or less even when the pulse irradiation is performed several times. In addition, the fluorescence lifetime T of the light-emitting unit 10 is set to 430 nsec or more, so that 10% or more the emission intensity can be measured, a sufficient signal strength can be obtained, and thus the measurement accuracy can be improved.

Sixth Embodiment

Figure 9:
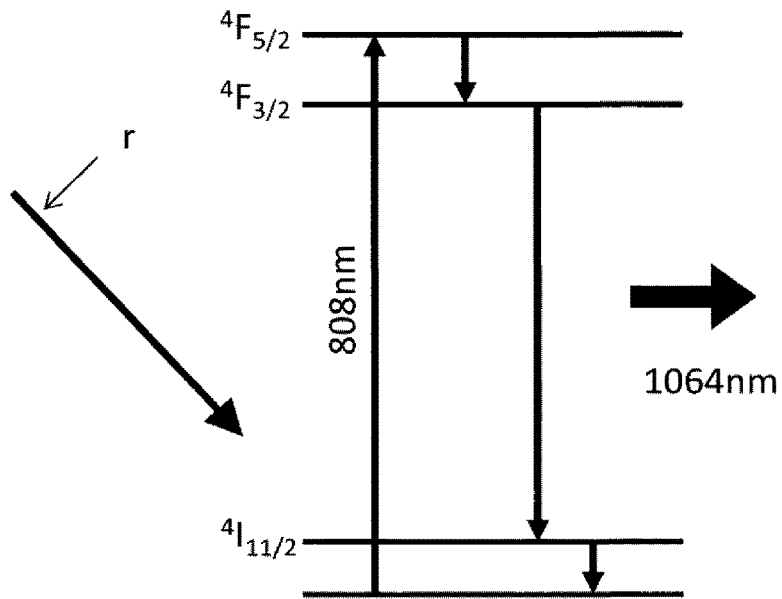
FIG. 9 is a conceptual diagram illustrating a procedure of generating a photon using a radiation incident on the light-emitting unit of a Nd:YAG crystal according to a sixth embodiment.

A radiation monitor according to a sixth embodiment will be described using FIG. 9. FIG. 9 is a conceptual diagram illustrating a procedure of generating a photon (light) using a radiation incident on the light-emitting unit of a Nd:YAG crystal according to this embodiment.

The radiation monitor in this embodiment has the same basic configuration as the radiation monitor of any one of the first to fourth embodiments. This embodiment is different from these embodiments only in that the light-emitting unit 10 is made of only a Nd-doped YAG (a crystal of a garnet structure made of a complex oxide of yttrium and aluminum ($Y_3Al_5O_{12}$)). The description will be given in detail only about the characteristic of the light-emitting unit 10.

Nd:YAG, which is a Nd-doped YAG crystal, is used widely as a laser material, and generally absorbs light having a wavelength band near 750 nm and 800 nm to discharge the light having a wavelength 1,064 nm with a fluorescence lifetime of about 230 psec.

The emission principle of Nd:YAG is illustrated in FIG. 9. As illustrated in FIG. 9, when the radiation is incident on Nd:YAG, the radiation and Nd:YAG interacts with each other, and the electron in the ground state is excited to an absorption band ($^4F_{5/2}$). The electron excited to the absorption band is non-radioactively shifted to the laser high level ($^4F_{3/2}$), and the photon (1,064 nm) is emitted when the electron is further shifted from the laser high level ($^4F_{3/2}$) to a laser low level ($^4I_{11/2}$) with a low excitation energy. The electron is excited not only by the radiation but also by the light interaction, and the wavelength is mainly 808 nm.

In addition, as described above, the inventors have experimentally confirmed that there is a one-to-one correspondence as illustrated in FIG. 2 between the dose rate of the radiation incident on the light-emitting unit 10 of Nd:YAG and the number of photons per unit time which are generated by the light-emitting unit 10.

Therefore, the 1,064 nm photon emitted by the light-emitting unit 10 of Nd:YAG is sent up to the photoelectric converter 30 by the optical fiber 20. The photons are converted one by one into an electric pulse signal by the photoelectric converter 30. The photons are counted by the dose calculation device 40. Accordingly, the dose and the dose rate can be calculated. In addition, a variation of the counting rate of the photons and an irradiation timing signal from the radiation irradiation device 60 are received to determine the radiation timing. The emission of the light-emitting unit 10 except the radiation timing is measured to remove the Cherenkov radiation.

Further, the optical filter 70 is disposed between the light-emitting unit 10 of Nd:YAG and the optical fiber 20, so that the incidence of the Cherenkov radiation on the light-emitting unit 10 of Nd:YAG is blocked, and the indirect influence of the Cherenkov radiation can be removed.

In the radiation monitor of this embodiment, the Nd:YAG crystal is used as the light-emitting unit 10, so that the dose and the dose rate can be measured with high accuracy while removing the Cherenkov radiation.

Seventh Embodiment

A radiation monitor according to a seventh embodiment will be described.

The radiation monitor in this embodiment has the same basic configuration as the radiation monitor of the sixth embodiment. The feature of this embodiment is that the blocking wavelength of the optical filter 70, which is a long pass filter, is equal to or more than 808 nm and less than 1,064 nm. The details will be described below.

As described in the sixth embodiment, the main absorption wavelength of Nd:YAG is 808 nm, and the emission wavelength is 1,064 nm. Therefore, the cutoff frequency of the optical filter 70 is set to be equal to or more than 808 nm at least, and the upper limit is set to be less than 1,064 nm, such that the 1,064 nm photon emitted from the light-emitting unit 10 of Nd:YAG are made to pass. In addition, the incidence of the Cherenkov radiation on the light-emitting unit 10 of Nd:YAG is blocked to more effectively suppress the emission caused by the Cherenkov radiation.

Further, as described above, the emission wavelength emitted from the light-emitting unit 10 of Nd:YAG is the light having a 1,064 nm wavelength, so that the cutoff frequency of the optical filter 70 is desirably set in consideration of the error.

In the radiation monitor of this embodiment, the Nd:YAG crystal is used as the light-emitting unit 10, a long pass filter having the blocking wavelength as the optical filter 70 of equal to or more than 808 nm and less than 1,064 nm is used. Therefore, the dose and the dose rate can be measured with high accuracy while removing the Cherenkov radiation.

Eighth Embodiment

Figure 10:
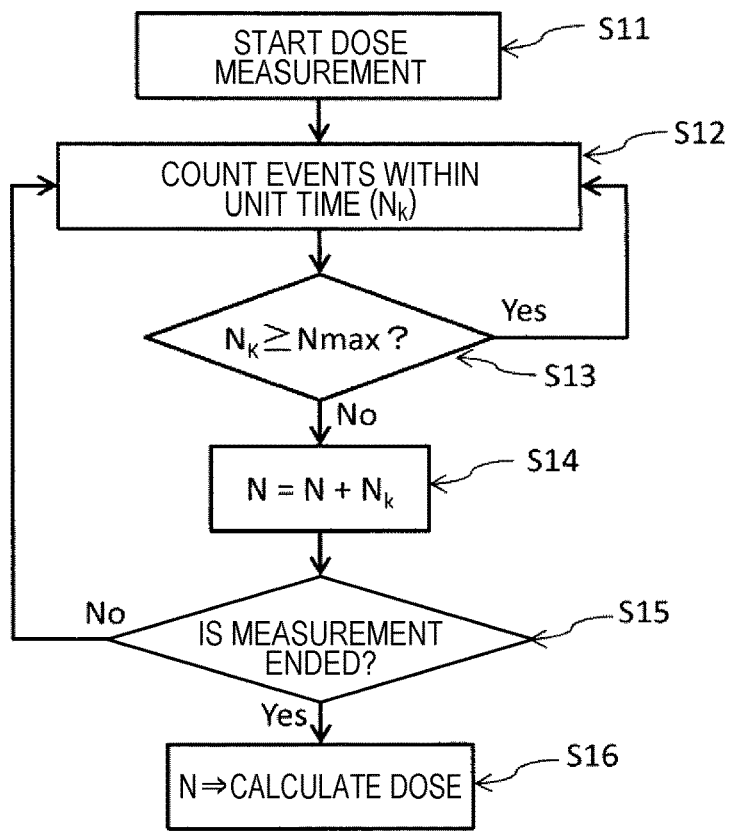
FIG. 10 is a flowchart of a radiation measurement control of a radiation monitor according to an eighth embodiment.

A method of monitoring the radiation according to an eighth embodiment will be described using FIG. 10. FIG. 10 is a flowchart of the radiation measurement control of a radiation monitor according to this embodiment.

The configuration of the radiation monitor according to this embodiment is similar to those of the radiation monitor of the first embodiment illustrated in FIG. 1, those of the radiation monitor of the third embodiment illustrated in FIG. 6, and those of the radiation monitors of the fourth, fifth, sixth, and seventh embodiments, and thus the description thereof will be omitted.

A method of monitoring the radiation according to this embodiment will be described using a flowchart of FIG. 10. This processing flow is a control process flow which is mainly performed by the dose calculation device 40.

<Step 1 (Step S11)>

The radiation starts by an operator's operation, and the dose measurement starts.

<Step 2 (Step S12)>

First, after the counted number $N_k$ is reset to 0, the photons are counted by the light-emitting unit 10, the optical fiber 20, the photoelectric converter 30, and the dose calculation device 40, and the counted number ($N_k$) within a predetermined unit time is measured. Herein, k represents an execution number of the counting within the unit time.

<Step 3 (Step S13)>

Next, a maximum counted number (Nmax) which is set and held in advance is compared with the counted number ($N_k$), and it is determined whether $N_k$ is equal to or more than Nmax. If it is determined that $N_k$ is equal to or more than Nmax, the counting is determined to be performed during the irradiation, and the process returns to Step S12 without adding the counts. On the other hand, if it is determined that $N_k$ is less than Nmax, the process proceeds to the next Step S14.

Figure 5:
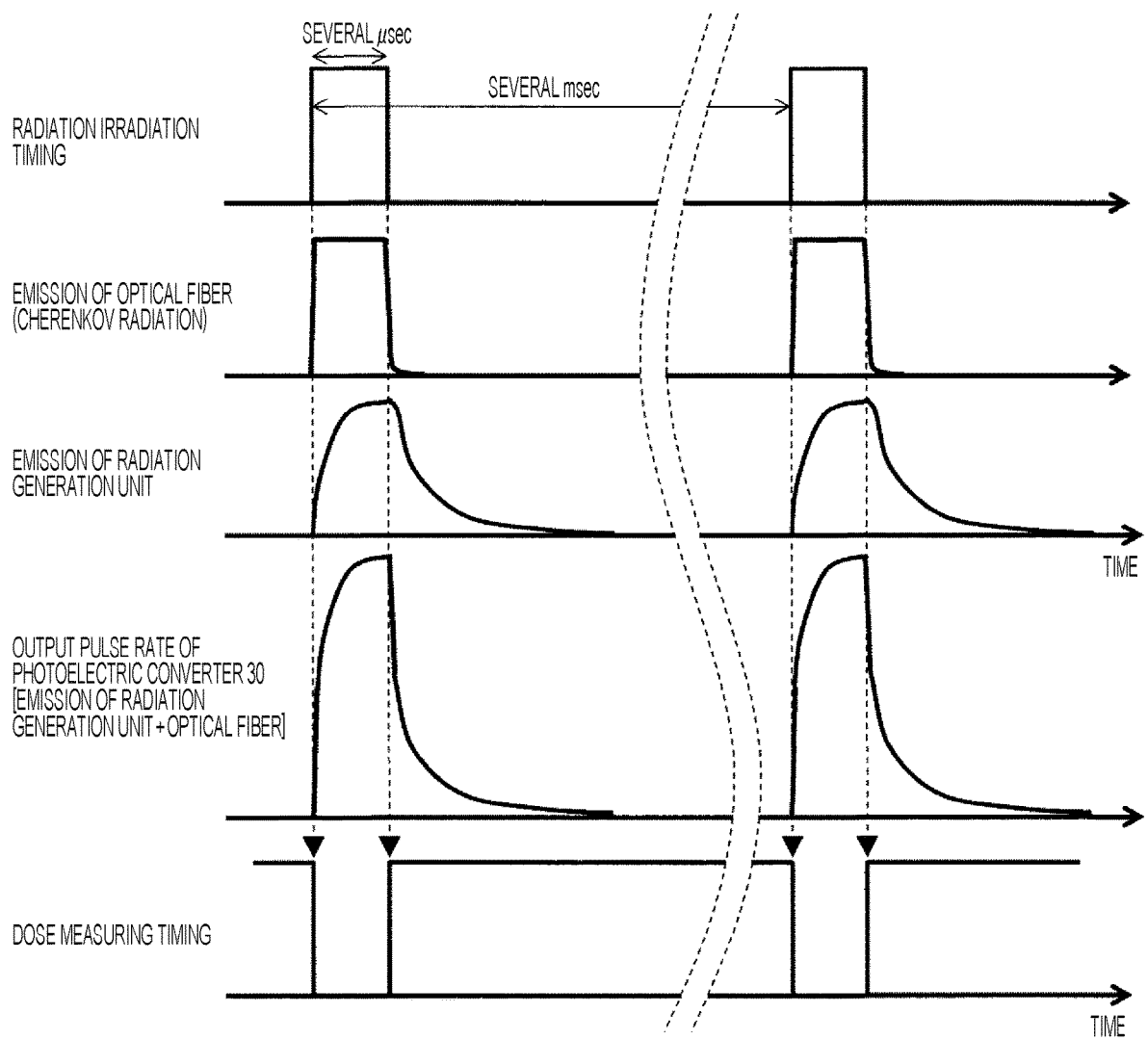
FIG. 5 is a timing chart of a radiation timing, the Cherenkov radiation, an emission state of a light-emitting unit, and the like according to the second embodiment.

Herein, the maximum counted number Nmax is a value obtained in advance through experiences, and can be a value linked to the radiation dose of the irradiation plan, and corresponds to the measurement timing threshold in FIGS. 3 and 5.

<Step 4 (Step S14)>

$N_k$ measured in Step S12 is added to the total counted number N.

<Step 5 (Step S15)>

It is determined whether a predetermined measurement end condition (for example, irradiation time) is satisfied. If it is determined that the measurement end condition is not satisfied, the process proceeds to Step S12, and the measurement continues. On the other hand, if it is determined that the measurement end condition is satisfied, the process proceeds to the next Step S16.

<Step 6 (Step S16)>

The dose or the dose rate is calculated using a conversion table (conversion equation) which is held in advance from the measured total counted number N, the result is displayed on the display device 50, and the measurement ends.

According to the processing flow in this embodiment, the irradiation timing can be specified while monitoring the counted number within the unit time. When the irradiation timing is specified, it is possible to realize a high accuracy measurement of the dose or the dose rate while reducing the influence of the Cherenkov radiation without measurement. In addition, there is no need of a specific measurement unit other than the dose measurement unit. Therefore, it is possible to realize the simplified device at a low cost.

Ninth Embodiment

Figure 11:
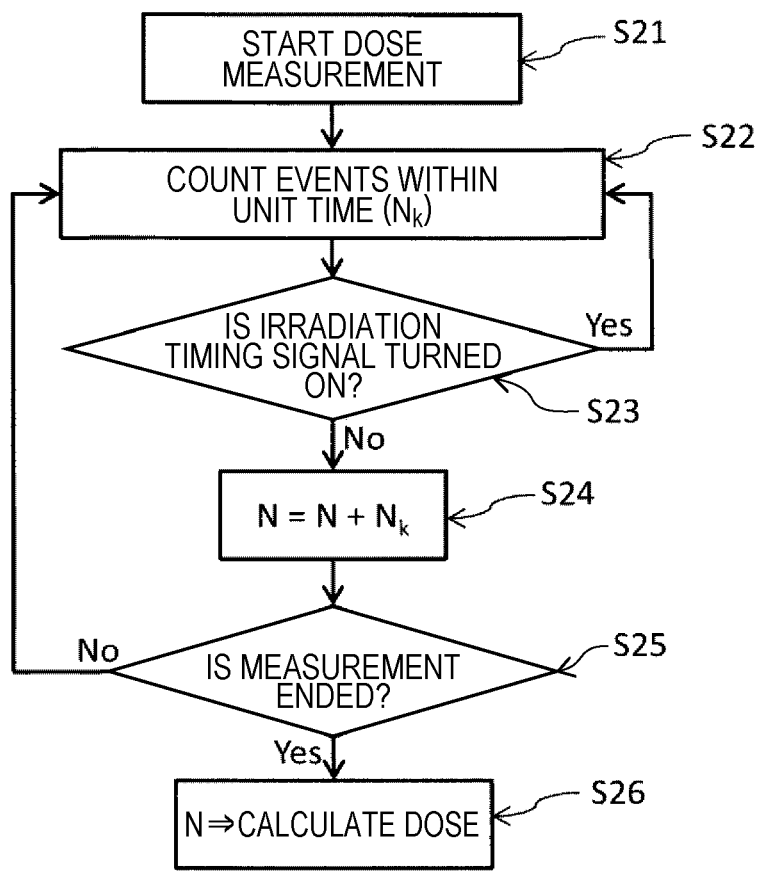
FIG. 11 is a flowchart of the radiation measurement control of a radiation monitor according to a ninth embodiment.

A method of monitoring the radiation of a ninth embodiment will be described using FIG. 11. FIG. 11 is a flowchart of the radiation measurement control of a radiation monitor according to this embodiment.

The configuration of the radiation monitor according to this embodiment is similar to that of the radiation monitor of the second embodiment illustrated in FIG. 4, that of the radiation monitor of the third embodiment illustrated in FIG. 6, and those of the radiation monitors of the fourth, fifth, sixth, and seventh embodiments, and thus the description will be omitted.

A method of monitoring the radiation according to this embodiment will be described using a flowchart of FIG. 11. This processing flow is a control process flow which is mainly performed by the dose calculation device 40.

<Step 1 (Step S21)>

The radiation starts by an operator's operation, and the dose measurement starts.

<Step 2 (Step S22)>

First, after the counted number $N_k$ is reset to 0, the photons are counted by the light-emitting unit 10, the optical fiber 20, the photoelectric converter 30, and the dose calculation device 40, and the counted number ($N_k$) within a predetermined unit time is measured. Herein, k represents an execution number of the counting within the unit time. Further, the maximum counted number Nmax corresponds to the measurement timing threshold in FIGS. 3 and 5 similarly to the eighth embodiment.

<Step 3 (Step S23)>

Next, it is determined whether the irradiation timing signal is turned ON (high). If it is determined that the irradiation timing signal is turned ON, the counting is determined to be performed during the irradiation, and the process returns to Step S22 without adding the counts. On the other hand, if it is determined that the irradiation timing signal is not turned ON, the process proceeds to the next Step S24.

<Step 4 (Step S24)>

$N_k$ measured in Step S22 is added to the total counted number N.

<Step 5 (Step S25)>

It is determined whether a predetermined measurement end condition (for example, irradiation time) is satisfied. If it is determined that the measurement end condition is not satisfied, the process proceeds to Step S22, and the measurement continues. On the other hand, if it is determined that the measurement end condition is satisfied, the process proceeds to the next Step S26.

<Step 6 (Step S26)>

The dose or the dose rate is calculated using a conversion table (conversion equation) which is held in advance from the measured total counted number N, the result is displayed on the display device 50, and the measurement ends.

Further, the measurement method when the irradiation timing signal is turned ON is not limited to this processing flow. When the irradiation timing signal is turned ON, the process is simply performed not to perform the counting (adding).

According to the processing flow in this embodiment, the irradiation timing of the radiation can be specified from the irradiation timing signal, and the irradiation timing (that is, the occurrence timing of the Cherenkov radiation) can be specified with accuracy. Therefore, it is possible to realize a high accuracy measurement of the dose and the dose rate while further reducing the influence of the Cherenkov radiation.

<Others>

Further, the invention is not limited to the above embodiments, and various modifications may be contained. The above-described embodiments have been described in detail for clear understating of the invention, and are not necessarily limited to those having all the described configurations. In addition, some of the configurations of a certain embodiment may be replaced with the configurations of the other embodiments, and the configurations of the other embodiments may be added to the configurations of the subject embodiment. In addition, some of the configurations of each embodiment may be omitted, replaced with other configurations, and added to other configurations.

REFERENCE SIGNS LIST 1, 1a, 1b radiation monitor
10 light-emitting unit
20 optical fiber
30 photoelectric converter
40, 40a dose calculation device
42 memory device
50 display device
60 radiation irradiation device
70 optical filter

The invention claimed is:

1. A radiation monitor, comprising:
   a light-emitting unit which generates light having an intensity depending on an amount of incident radiation;
   an optical fiber which sends a photon generated by the light-emitting unit;
   a photoelectric converter which converts the photon sent by the optical fiber into an electric signal;
   a dose calculation device which calculates a dose from the electric signal converted by the photoelectric converter, detects a radiation timing and calculates a dose of the radiation on the basis of the detected timing; and
   a display device which displays a measurement result calculated by the dose calculation device,
   wherein an optical filter is disposed between the light-emitting unit and the optical fiber, and
   wherein the optical filter blocks light having a wavelength equal to or less than a cutoff wavelength.

2. The radiation monitor according to claim 1,
   wherein the dose calculation device counts an electric signal converted from each one of the photon by the photoelectric converter one by one to calculate a counting rate, and detects the radiation timing from the counting rate to control an addition timing of counts used in the calculation of the dose.

3. The radiation monitor according to claim 1,
   wherein the dose calculation device receives an irradiation timing signal from a radiation device which irradiates the radiation, and detects the irradiation timing from the irradiation timing signal to control an addition timing of counts used in the calculation of the dose.

4. The radiation monitor according to claim 1,
   wherein the light-emitting unit has a fluorescence lifetime of 430 nsec or more and 2.8 msec or less.

5. The radiation monitor according to claim 1,
   wherein the light-emitting unit is a Nd-doped YAG crystal.

6. The radiation monitor according to claim 5,
   wherein the cutoff wavelength of the optical filter is a value falling within a range of 808 nm or more and less than 1,064 nm.

7. A method of monitoring a radiation, comprising:
   irradiating light having an intensity depending on an amount of an incident radiation;
   sending a photon generated in the irradiating through an optical fiber;
   converting the photon sent through the optical fiber into an electric signal; and
   detecting a radiation timing and calculating a dose of the radiation on the basis of the detected timing from the electric signal converted in the converting,
   wherein an optical filter is disposed between the light-emitting unit and the optical fiber, and
   wherein the optical filter blocks light having a wavelength equal to or less than a cutoff wavelength.

8. The method of monitoring a radiation according to claim 7,
   wherein the calculating counts an electric signal converted from each one of the photons in the converting one by one to calculate a counting rate, and detects a radiation timing from the counting rate to adjust an addition timing of counts used in the calculation of the dose.

9. The method of monitoring of the radiation according to claim 7,
   wherein the calculating receives an irradiation timing signal from a radiation irradiation device which irradiates the radiation, and detects the irradiation timing from the irradiation timing signal to adjust an addition timing of counts used in the calculation of the dose.

* * * * *